(12) United States Patent
Pietronigro et al.

(10) Patent No.: US 7,893,045 B2
(45) Date of Patent: *Feb. 22, 2011

(54) METHODS FOR TREATING LYMPHOMAS IN CERTAIN PATIENT POPULATIONS AND SCREENING PATIENTS FOR SAID THERAPY

(75) Inventors: Dennis Pietronigro, Clinton, NJ (US); Annette Ervin-Hayes, Watchung, NJ (US); Jerome B. Zeldis, Princeton, NJ (US)

(73) Assignee: Celgene Corporation, Summit, NJ (US)

( * ) Notice: Subject to any disclaimer, the term of this patent is extended or adjusted under 35 U.S.C. 154(b) by 131 days.

This patent is subject to a terminal disclaimer.

(21) Appl. No.: 12/221,651

(22) Filed: Aug. 5, 2008

(65) Prior Publication Data

US 2009/0081203 A1 Mar. 26, 2009

Related U.S. Application Data (60) Provisional application No. 60/963,973, filed on Aug. 7, 2007, provisional application No. 60/965,202, filed on Aug. 17, 2007.

(51) Int. Cl.
*A01N 43/00* (2006.01)

(52) U.S. Cl. ..................................... 514/183

(58) Field of Classification Search ........................ None
See application file for complete search history.

(56) References Cited

U.S. PATENT DOCUMENTS

| | | | |
|---|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,810,643 A | 3/1989 | Souza |
| 4,999,291 A | 3/1991 | Souza |
| 5,059,595 A | 10/1991 | Le Grazie |
| 5,073,543 A | 12/1991 | Marshall et al. |
| 5,120,548 A | 6/1992 | McClelland et al. |
| 5,134,127 A | 7/1992 | Stella et al. |
| 5,229,496 A | 7/1993 | Deeley et al. |
| 5,354,556 A | 10/1994 | Sparks et al. |
| 5,385,901 A | 1/1995 | Kaplan et al. |
| 5,391,485 A | 2/1995 | Deeley et al. |
| 5,393,870 A | 2/1995 | Deeley et al. |
| 5,528,823 A | 6/1996 | Rudy, Jr. et al. |
| 5,580,755 A | 12/1996 | Souza |
| 5,591,767 A | 1/1997 | Mohr et al. |
| 5,593,990 A | 1/1997 | D'Amato |
| 5,629,327 A | 5/1997 | D'Amato |
| 5,635,517 A | 6/1997 | Muller et al. |
| 5,639,476 A | 6/1997 | Oshlack et al. |
| 5,674,533 A | 10/1997 | Santus et al. |
| 5,698,579 A | 12/1997 | Muller |
| 5,712,291 A | 1/1998 | D'Amato |
| 5,731,325 A | 3/1998 | Andrulis, Jr. et al. |
| 5,733,566 A | 3/1998 | Lewis |
| 5,798,368 A | 8/1998 | Muller et al. |
| 5,874,448 A | 2/1999 | Muller et al. |
| 5,877,200 A | 3/1999 | Muller |
| 5,929,117 A | 7/1999 | Muller et al. |
| 5,955,476 A | 9/1999 | Muller et al. |
| 6,020,358 A | 2/2000 | Muller et al. |
| 6,071,948 A | 6/2000 | D'Amato |
| 6,114,355 A | 9/2000 | D'Amato |
| 6,140,346 A | 10/2000 | Andrulis, Jr. et al. |
| 6,228,879 B1 | 5/2001 | Green et al. |
| 6,235,756 B1 | 5/2001 | D'Amato |
| 6,281,230 B1 | 8/2001 | Muller et al. |
| 6,316,471 B1 | 11/2001 | Muller et al. |
| 6,326,388 B1 | 12/2001 | Man et al. |
| 6,335,349 B1 | 1/2002 | Muller et al. |
| 6,380,239 B1 | 4/2002 | Muller et al. |
| 6,395,754 B1 | 5/2002 | Muller et al. |
| 6,403,613 B1 | 6/2002 | Man et al. |
| 6,420,414 B1 | 7/2002 | D'Amato |
| 6,458,810 B1 | 10/2002 | Muller et al. |
| 6,469,045 B1 | 10/2002 | D'Amato |

(Continued)

FOREIGN PATENT DOCUMENTS

WO 19065 * 2/2008

OTHER PUBLICATIONS

Wilzig, Thomas E. et al., "Early Results from a Phase II Study of Lenalidomide Monotherapy in Relapsed/Refractory Indolent Non-Hodgkin's Lymphoma," *Blood* (ASH Annual Meetings Abstracts), 2006, 108:Abstract 2482.

(Continued)

*Primary Examiner*—Sheela J Huff
(74) *Attorney, Agent, or Firm*—Jones Day (57) ABSTRACT

Methods for predicting a response of a patient having a lymphoma to a therapy regimen of 3-(4-amino-1-oxo-1,3-dihydro-isoindol-2-yl)-piperidine-2,6-dione using prognostic factors of a patient's disease burden, absolute lymphocyte count or time since last rituximab therapy are disclosed. Specific methods of treating a lymphoma encompass the administration of 3-(4-amino-1-oxo-1,3-dihydro-isoindol-2-yl)-piperidine-2,6-dione to a patient who has one or more of the favorable profiles, alone or in combination with immunosuppressive agents such as rituximab.

25 Claims, 1 Drawing Sheet

U.S. PATENT DOCUMENTS

| | | | |
|---|---|---|---|
| 6,476,052 | B1 | 11/2002 | Muller et al. |
| 6,518,298 | B2 | 2/2003 | Green et al. |
| 6,555,554 | B2 | 4/2003 | Muller et al. |
| 6,673,828 | B1 | 1/2004 | Green et al. |
| 2001/0018445 | A1 | 8/2001 | Huang et al. |
| 2001/0056114 | A1 | 12/2001 | D'Amato |
| 2002/0035090 | A1 | 3/2002 | Zeldis et al. |
| 2002/0045643 | A1 | 4/2002 | Muller et al. |
| 2002/0052398 | A1 | 5/2002 | D'Amato |
| 2002/0054899 | A1 | 5/2002 | Zeldis |
| 2002/0061923 | A1 | 5/2002 | D'Amato |
| 2002/0128228 | A1 | 9/2002 | Hwu |
| 2002/0161023 | A1 | 10/2002 | D'Amato |
| 2002/0173658 | A1 | 11/2002 | Muller et al. |
| 2002/0183360 | A1 | 12/2002 | Muller et al. |
| 2003/0013739 | A1 | 1/2003 | Masferrer et al. |
| 2003/0028028 | A1 | 2/2003 | Man et al. |
| 2003/0045552 | A1 | 3/2003 | Robarge et al. |
| 2003/0069428 | A1 | 4/2003 | Muller et al. |
| 2003/0096841 | A1 | 5/2003 | Robarge et al. |
| 2003/0139451 | A1 | 7/2003 | Shah et al. |
| 2003/0144325 | A1 | 7/2003 | Muller et al. |
| 2003/0181428 | A1 | 9/2003 | Green et al. |
| 2003/0187024 | A1 | 10/2003 | D'Amato |
| 2003/0191098 | A1 | 10/2003 | D'Amato |
| 2003/0235909 | A1 | 12/2003 | Hariri et al. |
| 2004/0029832 | A1 | 2/2004 | Zeldis |
| 2004/0077685 | A1 | 4/2004 | Figg et al. |
| 2004/0077686 | A1 | 4/2004 | Dannenberg et al. |
| 2004/0087546 | A1 | 5/2004 | Zeldis |
| 2004/0091455 | A1 | 5/2004 | Zeldis |
| 2004/0122052 | A1 | 6/2004 | Muller et al. |

OTHER PUBLICATIONS

International Search Report for PCT/US2008/009393 dated Nov. 6, 2008.

Zhang et al., "Direct Inhibitory Effects on Lenatidomide on the Proliferation and VEGF Production of Non-Hodgkin Lymphoma Cells are Associated with Increased SPARC Expression," *Blood* (ASH Annual Meeting Abstracts), Nov. 2008, 112:2612.

Zhang et al., "Tumoricidal activity of lenalidomide against hematologic tumor cells correlates with cyclin D1/D2 expression and leads to tumor suppressor gene up-regulation," *J Clin Oncol* (ASCO Annual Meeting Abstracts), 2008, 26:22150.

Zhang et al., "Lenalidomide Displays Direct Anti-non-Hodgkin's Lymphoma (NHL) Cell Activity in Association With Enhanced SPARC Expression but Independent of Its Inability to Strongly Inhibit NHL Cell VEGF Production In Vitro," *Blood* (ASH Annual Meeting Abstracts), Nov. 2007, 110:3473.

Anolik JH, Friedberg JW, Zheng B, et al: B cell reconstitution after rituximab treatment of lymphoma recapitulates B cell ontogeny. *Clin Immunol* 2007; 122:139-145.

Bartlett JB, Michael A, Clarke IA, et al. Phase I study to determine the safety, tolerability and immunostimulatory activity of thalidomide analogue CC-5013 in patients with metastatic malignant melanoma and other advanced cancers. *Br J Cancer* 2004; 90: 955-961.

Bouaziz J, Yanaba K, Venturi GM, et al. Therapeutic B cell depletion impairs adaptive and autoreactive CD4$^+$T cell activation in mice. *Proc Natl Acad Sci* 2007; 104:20878-20883.

Buesche G, Dieck S, Giagounidis A, et al. Anti-angiogenic in vivo effect of lenalidomide (CC-5013) in myelodysplastic syndrome with del(5q) chromosome abnormality and its relation to the course of disease. *Blood* 2005; 106: 372a.

Coiffier B, Haioun N, Ketterer N, et al: Rituximab (anti-CD20 monoclonal antibody) for the treatment of patients with relapsing or refractory aggressive lymphoma: a multicenter phase II study. *Blood* 1998; 92:1927-1932.

Corral LG, Haslett PAJ, Muller GW, et al. Differential cytokine modulation and T cell activation by two distincy classes of thalidomide analogues that are potent inhibitors of TNF-α. *The Journal of Immunology* 1999; 163: 380-386.

Crawford A, MacLeod M, Schumacher T, et al. Primary T Cell expansion and differential in vivo requires antigen presentation by B cells. *The Journal of Immunology* 2006; 176:3498-3506.

Devizzi L, Santoro A, Bonfante V, et al. Vinorelbine: an active drug in the management of patients with heavily pretreated Hodgkin's disease. *Ann Oncol* 1994; 5: 817-20.

Dredge K, Marriott JB, Macdonald CD, et al. Novel thalidomide analogues display anti-angiogenic activity independently of immunomodulatory effects. *Br J Cancer* 2002; 87: 1166-1172.

Dredge K, Horsfall R, Robinson S, et al. Orally administered lenalidomide (CC-5013) is anti-angiogenic in vivo and inhibits endothelial cell migration and Akt phosphorylation in vitro. *Microvascular Research* 2005; 69: 56-63.

Epner EM, Unger J, Miller T, Rimzsa L, Spier C, Leblanc M. A multi center trial of hyper CVAD=Rituxan in patients with newly diagnosed mantle cell lymphoma [abstract #387]. *Blood* 2007; 110.

Fisher RI, Bernstein SH, Kahl BS, et al. Multicenter phase II study of bortezomib in patients with relapsed or refractory mantle cell lymphoma. *J Clin Oncol* 2006; 24: 4867-4874.

Fosså A, Santoro A, Hiddemann W, et al: Gemcitabine as a single agent in the treatment of relapsed or refractory aggressive non-Hodgkin's lymphoma. *J Clin Oncol* 1999; 17:3786-3792.

Geisler CH, Elonen E, Kolstad A, et al. Mantle Cell Lymphoma Can Be Cured by Intensive Immunochemotherapy with In-Vivo Purged Stem-Cell Support; Final Report of the Nordic Lymphoma Group MCL2 Study. Abstract LB1. Presented at the annual meeting of the ASH, Dec. 2007.

Ghielmini M, Schmitz SF, Cogliatti S, et al. Effect of single-agent rituximab given at the standard schedule or as prolonged treatment in patients with mantle cell lymphoma: a study of the Swiss Group for Clinical Cancer Research (SAKK). *J Clin Oncol.* 2005; 23: 705-11.

Gordan LN, Sugrue MW, Lynch JW, Williams KD, Khan SA, Moreb JS. Correlation of early lymphocyte recovery and progression-free survival after autologous stem-cell transplant in patients with Hodgkin's and non-Hodgkin's Lymphoma [abstract]. *Bone Marrow Transplantation* 2003; 31: 1009-1013, Abstract.

Goy A, Younes A, McLaughlin P, et al: Phase II study of proteasome inhibitor bortezomib in relapsed or refractory B-cell non-Hodgkin's lymphoma. *J Clin Oncol* 2005; 23: 667-675.

Hamlin PA, Zelenetz AD, Kewalramani T, et al. Age-adjusted International Prognostic Index predicts autologous stem cell transplantation outcome for patients with relapsed or primary refractory diffuse large B-cell lymphoma. *Blood* 2003; 102: 1989-1996.

Hideshima T, Chauhan D, Shima Y, et al. Thalidomide and its analogs overcome drug resistance of human multiple myeloma cells to conventional therapy. *Blood* 2000; 96: 2943-2950.

Horna P, Cuenca A, Cheng F, et al. In vivo disruption of tolerogenic cross-presentation mechanisms uncovers an effective T-cell activation by V-cell lymphomas leading to antitumor immunity. *Blood* 2006; 107: 2871-2878.

Kewalramani T, Nimer SD, Zelenetz AD, et al. Progressive disease following autologous transplantation in patients with chemosensitive relapsed or primary refractory Hodgkin's disease or aggressive non-Hodgkin's lymphoma. *Bone Marrow Transplantation* 2003; 32: 673-679.

Küppers R, Rajewsky K, Zhao M, et al. Hodgkin disease: Hodgkin and Reed-Sternberg cells picked from histological sections show clonal immunoglobulin gene rearrangements and appear to be derived from B cells at various stages of development. *Proc Natl Acad Sci* 1994; 91: 10962-10966.

Linch DC, Winfield D, Goldstone AH, et al. Dose intensification with autologous bone-marrow transplantation in relapsed and resistant Hodgkin's disease: Results of a BNLI randomised trial. *Lancet* 1993; 341: 1051-1054.

Little R, Wittes RE, Longo DL et al. Vinblastine for recurrent Hodgkin's disease following autologous bone marrow transplant. *J Clin Oncol* 1998; 16:584-588.

Lossos IS, Wiernik PH, Justice G, et al. Lenalidomide Response in Relapsed/Refractory Diffuse Large B-Cell Non-Hodgkin's Lymphoma. *Blood (Ash Annual Meeting Abstracts)*, Nov. 2007; 110: 2564.

Menard LC, Minns LA, Darche S, et al. B cells amplify IFN-γ Production by T cells via a TNF-α-mediated mechanism. *The Journal of Immunology* 2007; 179: 4857-4866.

Morschhauser F, Seymour JF, Kluin-Nelemans HC, et al. A phase II study of enzastaurin, a protein kinase C beta inhibitor, in patients with relapsed or refractory mantle cell lymphoma. *Ann Oncol*. Sep. 28, 2007.

Moskowitz CH, Zelenetz AD, Kewalramani T, et al. Cell of origin, germinal center versus nongerminal center, determined by immunohistochemistry on tissue microarray, does not correlate with outcome in patients with relapsed and refractory DLBCL. *Blood* 2005; 106:3383-3385.

Moskowitz CH. Pretreatment prognostic factors and outcome in patients with relapsed or primary-refractory diffuse large B-cell lymphoma treated with second-line chemotherapy and autologous stem cell transplantation. *Ann Oncol* 2006; 17: 1v37-iv39.

Paltiel O, Rubinstein C, Or R, et al. Factors associated with survival in patients with progressive disease following autologous transplant for lymphoma. *Bone Marrow Transplant* 2003; 31: 565-569.

Pan D, Moskowitz CH, Zelenetz AD, et al. Rituximab for aggressive non-Hodgkin's lymphomas relapsing after or refractory to autologous stem cell transplantation. *Cancer J.* 2002; 8: 371-376.

Pfreundschuh MG, Hensel M, Cavallin-Stahl E, et al: Prognostic significance of maximal tumour size (MTS) in young patients with good-prognosis diffuse large B-cell lymphoma (DLBCL) treated with CHOP-like chemotherapy with and without rituximab: Analysis of the MabThera International Trial Group (MInT) study. *J Clin Oncol* 2007; 25:18s (suppl; abstr 8053).

Porrata LD, Litzow MR, Inwards DJ, et al. Infused peripheral blood autograft absolute lymphocyte count correlates with day 15 absolute lymphocyte count and clinical outcome after autologous peripheral hematopoietic stem cell transplantation in non-Hodgkin's lymphoma [abstract]. *Bone Marrow Transplantation* 2004; 33: 291-298, Abstract.

Rule A, Tighe M. Davies S and Johnson S. Vinorelbine in the treatment of lymphoma. *Hematol Oncol* 1998; 16: 101-105.

Schafer PH, Gandhi AK, Loveland MA, et al. Enhancement of cytokine production and AP-1 transcriptional activity in T cells by thalidomide-related immunomodulatory drugs. *JPET* 2003; 305: 1222-1232.

Schmitz N, Pfistner B, Sextro M et al. Aggressive conventional chemotherapy compared with high-dose chemotherapy with autologous haemopoietic stem-cell transplantation for relapsed chemosensitive Hodgkin's disease: A randomised trial. *Lancet* 2002; 359: 2065-2071.

Stasi R, Brunetti M, Stipa E, et al: Selective B-cell depletion with rituximab for the treatment of patients with acquired hemophilia. *Blood* 2004; 103:4424-4428.

Stasi R, Del Poeta G, Stipa E, et al. Response to B-cell depleting therapy with rituximab reverts the abnormalities of T-cell subsets in patients with idiopathic thrombocytopenic purpura. *Blood* 2007; 110: 2924-2930.

Stewart DA, Bahlis N, Valentine K, et al: Upfront double high-dose chemotherapy with DICEP followed by BEAM and autologous stem cell transplantation for poor-prognosis aggressive non-Hodgkin lymphoma. *Blood* 2006; 107:4623-4627.

Tiwari D, Gao F, Hidalgo J, et al. Prognostic significance of early lymphocyte recovery after post-autografting administration of GM-CSF in non-Hodgkin's lymphoma [abstract]. *Bone Marrow Transplantation* 2007; 40: 671-675; Abstract.

Tobinai K, Watanabe T, Ogura M, et al. Phase II study of oral fludarabine phosphate in relapsed indolent B-cell non-Hodkin's lymphoma. *J Clin Oncol* 2006; 24: 174-180.

Tuscano JM, Lossos IS, Justice G, et al. Lenalidomide Oral Monotherapy Produces a 53% Response Rate in Patients with Relapsed/Refractory Mantle-Cell Non-Hodgkins Lymphoma. *Blood (ASH Annual Meeting Abstracts)*, Nov. 2007; 110: 2563.

Vallerskog T, Gunnarsson I, Widhe M, et al: Treatment with rituximab affects both the cellular and the humoral arm of the immune system in patients with SLE. *Clin Immuno* 2007; 122:62-74.

Verhelle D, Corral LG, Wong K, et al: Lenalidomide and CC-4047 inhibit the proliferation of malignant B cells while expanding normal CD34+progenitor cells. *Cancer Res* 2007; 67:746-755.

Vose JM, Bierman PJ, Anderson JR, et al. Progressive disease after high-dose therapy and autologous transplantation for lymphoid malignancy: Clinical course and patient follow-up. *Blood* 1992; 80: 2142-2148.

Vose JM, Bierman PJ, Lynch JC, et al: Effect of follicularity on autologous transplantation for large-cell non-Hodgkin's lymphoma. *J Clin Oncol* 1998; 16:844-849.

Vose JM, Tuscano JM, Justice G, et al. High Response Rate to Lenalidomide in Relapsed/Refractory Aggressive Non-Hodgkin's Lymphoma with Prior Stem Cell Transplant. *Blood (ASH Annual Meeting Abstracts)*, Nov. 2007; 110: 2570.

Wiemik PH, Lossos IS, Tuscano JM, et al. Lenalidomide Response in Relapsed/Refractory Aggressive Non-Hodgkin's Lymphoma is Related to Tumor Burden and Time from Rituximab Treatment. *Blood (ASH Annual Meeting Abstracts)*, Nov. 2007; 110: 2565.

Witzig TE, Geyer SM, Ghobrial I, et al. Phase II trial of sing-agent Temsirolimus (CCI-779) for relapsed mantle cell lymphoma. *J Clin Oncol* 2005; 23: 5347-5356.

Witzig TE, Reeder CB, Polikoff J, et al. Initial Results from an International Study in Relapsed/Refractory Aggressive Non-Hodgkin's Lymphoma to Confirm the Activity, Safety and Criteria for Predicting Response to Lenalidomide Monotherapy. *Blood (ASH Annual Meeting Abstracts)*, Nov. 2007; 110: 2572.

Zelenetz AD. Mantle cell lymphoma: an update on management. *Ann Oncol* 2006; 17: iv12-iv14.

Lentzsch et al., "S-3-Amino-phthalimido-glutarimide Inhibits Angiogenesis and Growth of B-cell Neoplasias in Mice," *Cancer Research*, 2002, 62:2300-2305.

Database Pharmaml, "Celgene's Revimid an orphan drug, says FDA," XP002369094 retrieved from STN. Database accession No. 1659300, & Marketletter, Oct. 9, 2001.

Database NLDB, "Celgene drug promises activity in solid tumors," XP002369095 retrieved from STN. Database accession No. 2002:35280, & Marketletter, Jun. 18, 2001.

Richardson et al., "A Phase 1 study of oral CC5013, an immunomodulatory thalidomide (Thal) derivative, in patients with relapsed and refractory multiple myeloma (MM)," American Society of Hematology, Dec. 7-11, 2001, Abstract #3225.

D'Amato et al., "Mechanism of Action of Thalidomide and 3-Aminothalidomide in Multiple Myeloma," *Seminars in Oncology*, 2001, 28(6):597-601.

Official Communication in corresponding EP Patent Application No. 09004756.4 dated Dec. 28, 2009.

\* cited by examiner

METHODS FOR TREATING LYMPHOMAS IN CERTAIN PATIENT POPULATIONS AND SCREENING PATIENTS FOR SAID THERAPY

This application claims the benefit of U.S. provisional application No. 60/963,973, filed Aug. 7, 2007, and U.S. provisional application No. 60/965,202, filed Aug. 17, 2007, the entireties of which are incorporated by reference herein.

1. FIELD OF THE INVENTION

The present invention relates to methods of treating lymphomas, wherein patients are screened for treatment by measuring prognostic factors of disease or tumor burden, absolute lymphocyte count (ALC) or time since last rituximab therapy, and then patients having favorable values of the factors are treated with 3-(4-amino-1-oxo-1,3-dihydro-isoindol-2-yl)-piperidine-2,6-dione, which is also known as lenalidomide, Revlimid® or Revimid®. The invention also relates to a method for predicting the responsiveness of a patient having lymphoma to a therapy with 3-(4-amino-1-oxo-1,3-dihydro-isoindol-2-yl)-piperidine-2,6-dione using prognostic factors of disease or tumor burden, absolute lymphocyte count or time since last rituximab therapy. Specific methods of the invention comprise administering 3-(4-amino-1-oxo-1,3-dihydro-isoindol-2-yl)-piperidine-2,6-dione, in combination with one or more second active agents, and/or in combination with radiation therapy, blood transfusions, or surgery.

In particular, this invention encompasses methods of treating or managing lymphomas such as non-Hodgkin's lymphomas, including but not limited to, mantle cell lymphoma (MCL), follicular center lymphoma, diffuse large B-cell lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma, cutaneous B-Cell lymphoma, and mantle zone lymphoma, using the prognostic factors.

2. BACKGROUND OF THE INVENTION

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J. and Kale, D., *Immunology*, 17.1-17.12 (3rd ed., Mosby, St. Louis, Mo., 1993).

There is an enormous variety of cancers which are described in detail in the medical literature. Examples includes cancer of the blood, lung, colon, rectum, prostate, breast, brain, and intestine. The various forms of the cancers such as lymphomas are described in U.S. provisional application No. 60/380,842, filed May 17, 2002, the entireties of which are incorporated herein by reference (see, e.g., Section 2.2. Types of Cancers).

Lymphoma is a heterogenous group of neoplasms arising in the reticuloendothelial and lymphatic systems. *The Merck Manual*, 955 (17th ed. 1999). Non-Hodgkin's lymphoma (NHL) refers to malignant monoclonal proliferation of lymphoid cells in the immune system, including lymph nodes, bone marrow, spleen, liver and gastrointestinal (GI) tract. *The Merck Manual*, at 958.

Non-Hodgkin's lymphoma (NHL) is the fifth most common cancer for both men and women in the United States, with an estimated 63,190 new cases and 18,660 deaths in 2007. Jemal A, et al., *CA Cancer J Clin* 2007; 57(1):43-66. The probability of developing NHL increases with age and the incidence of NHL in the elderly has been steadily increasing in the past decade, causing concern with the aging trend of the US population. Id. Clarke C A, et al., *Cancer* 2002; 94(7):2015-2023.

The NHL classification embraces a heterogeneous group of diseases, originating from B and T lymphocytes, which can be clinically characterized as indolent, aggressive, or highly aggressive. Most patients with aggressive NHL have a diffuse large B-cell lymphoma (DLBCL). Cerny T, et al., *Ann Oncol* 2002; 13 Suppl 4:211-216.

Mantle-cell lymphoma (MCL) is a B-cell type lymphoma originating from the mantle zone of the lymph node. It accounts for 5-10% of all lymphomas and usually affects men over the age of 60. The MCL cells appear small with morphologic features similar to indolent lymphomas. For this reason, MCL was in the past grouped in the category of indolent lymphoma. However, the discovery of a characteristic chromosomal translocation involving the cyclin D1 gene, resulting in its unregulated overexpression, led to an improved ability to diagnose MCL and recognition that MCL had clinical behavior similar to aggressive lymphomas and one of the poorest survival rates among the lymphomas.

Peripheral T-cell lymphomas (PTCL) is a heterogenous group of neoplasms arising in the lymphatic systems. *The Merck Manual*, 955 (17th ed. 1999). Patients with T-cell lymphoma can present with disease in the head and neck region, but these tumors are less common than B-cell lymphomas. Siegel et. al., Review and current concepts. *J Clin Oncol* 2000 August; 18(15): 2908-25. In general, T-cell lymphomas involve the nodal regions, but skin involvement with cutaneous T-cell lymphomas can also occur. Extranodal NK/T-cell lymphomas specifically involve the nasal sinuses. These lymphomas are derived from mature T-cells and have been subdivided into a number of distinct pathologic entities.

Anticancer drugs cause rapid and persistent depletion of lymphocytes, possibly by direct apoptosis induction in mature T and B cells. K. Stahnke. et al., *Blood* 2001, 98:3066-3073. Absolute lymphocyte count (ALC) has been shown to be a prognostic factor in follicular non-Hodgkin's lymphoma and recent results have suggested that ALC at diagnosis is an important prognostic factor in diffuse large B-cell lymphoma. D. Kim et al., *Journal of Clinical Oncology*, 2007 ASCO Annual Meeting Proceedings Part I. Vol 25, No. 18S (June 20 Supplement), 2007: 8082.

While patients who achieve a complete remission after initial therapy have a good chance for cure, less than 10% of those who do not respond or relapse achieve a cure or a response lasting longer than 3 years. Cerny T, et al., *Ann Oncol* 2002; 13 Suppl 4:211-216.

Further, rituximab is known to deplete normal host B cells. M. Aklilu et al., *Annals of Oncology* 15:1109-1114, 2004. The long-term immunologic effects of B cell depletion with rituximab and the characteristics of the reconstituting B cell pool in lymphoma patients are not well defined, despite the widespread usage of this therapy. Jennifer H. Anolik et al., *Clinical Immunology*, vol. 122, issue 2, February 2007, pages 139-145.

The approach for patients with relapsed or refractory disease relies heavily on experimental treatments followed by stem cell transplantation, which may not be appropriate for patients with a poor performance status or advanced age. Therefore, a tremendous demand exists for new methods that can be used to treat patients with NHL.

3. SUMMARY OF THE INVENTION

This invention encompasses methods for screening or identifying cancer patients for treatment with 3-(4-amino-1-oxo-1,3-dihydro-isoindol-2-yl)-piperidine-2,6-dione. In particular, provided herein are methods for selecting patients having a higher response rate to a therapy with 3-(4-amino-1-oxo-1,3-dihydro-isoindol-2-yl)-piperidine-2,6-dione. Such characteristics include, but are not limited to, a disease (tumor) burden of less than 50 cm$^2$ and an absolute lymphocyte greater than $0.6 \times 10^9$/L. Further, the patients included within the methods are preferably patients who receive 3-(4-amino-1-oxo-1,3-dihydro-isoindol-2-yl)-piperidine-2,6-dione prior to receiving rituximab or other immunosupressive agents. For example, the patients included within the methods are patients who receive 3-(4-amino-1-oxo-1,3-dihydro-isoindol-2-yl)-piperidine-2,6-dione, for about 28 days to about one day prior to receiving rituximab or other immunosupressive agents. Further, the patients included within the methods are patients that have not been treated with rituximab prior to, or have not been treated with rituximab for more than 230 days prior to beginning a therapy with 3-(4-amino-1-oxo-1,3-dihydro-isoindol-2-yl)-piperidine-2,6-dione.

Also encompassed by the invention is a method for predicting the responsiveness of a patient having a lymphoma to a therapy with 3-(4-amino-1-oxo-1,3-dihydro-isoindol-2-yl)-piperidine-2,6-dione. The prediction is conducted using prognostic factors of disease (tumor) burden, absolute lymphocyte count (ALC), time since last rituximab therapy for lymphomas, or all of them.

In one embodiment, patients are measured for disease (tumor) burden, absolute lymphocyte count (ALC) or time since last rituximab therapy, and then treatment with 3-(4-amino-1-oxo-1,3-dihydro-isoindol-2-yl)-piperidine-2,6-dione is given to the patients who are screened to have preferred profiles. Such profiles are described in detail below.

In a specific embodiment, the invention encompasses a method of treating or managing lymphomas, which comprises administering a therapeutically effective amount of 3-(4-amino-1-oxo-1,3-dihydro-isoindol-2-yl)-piperidine-2,6-dione, or a pharmaceutically acceptable salt, isomer or solvate thereof, to a patient who has (1) a disease (tumor) burden of less than 50 cm$^2$, (2) an absolute lymphocyte greater than $0.6 \times 10^9$/L, or (3) not less than 230 days passed since last rituximab therapy. Preferred patients meet the criteria of two of (1), (2) and (3), and most preferably meet all of (1), (2) and (3).

This invention encompasses methods of treating or managing certain types of cancers, and methods of predicting patients' responses to therapy, using prognostic factors. Cancers within the scope of the present invention include, but are not limited to, primary and metastatic cancers, as well as cancers that are relapsed, refractory or resistant to conventional chemotherapy such as rituximab. In particular, methods of this invention encompass methods of treating or managing various forms of NHL such as mantle cell lymphoma (MCL), follicular center lymphoma, diffuse large B-cell lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL) and mantle zone lymphoma, including lymphomas that are relapsed, refractory or resistant.

5. DETAILED DESCRIPTION OF THE INVENTION

A first embodiment of the invention encompasses methods for identifying or selecting cancer patients for treatment with 3-(4-amino-1-oxo-1,3-dihydro-isoindol-2-yl)-piperidine-2,6-dione which encompass measuring disease (tumor) burden, absolute lymphocyte count (ALC) and time since last rituximab therapy, and treating patients having favorable values of one or more of the factors with 3-(4-amino-1-oxo-1,3-dihydro-isoindol-2-yl)-piperidine-2,6-dione.

Also encompassed by the invention is a method for predicting a lymphoma patient's response to a therapy regimen of 3-(4-amino-1-oxo-1,3-dihydro-isoindol-2-yl)-piperidine-2,6-dione, using one or more prognostic factors of disease (tumor) burden, absolute lymphocyte count (ALC), and time since last rituximab therapy.

One embodiment of the invention encompasses a method of treating or managing a lymphoma, which comprises administering to a patient having a lymphoma a therapeutically effective amount of 3-(4-amino-1-oxo-1,3-dihydro-isoindol-2-yl)-piperidine-2,6-dione, or a pharmaceutically acceptable salt, solvate (e.g., hydrate) or stereoisomer thereof, wherein said patient meets one or more of the following criteria: (1) a disease burden of less than 50 cm$^2$; (2) an absolute lymphocyte count greater than $0.6 \times 10^9$/L; and (3) not less than 230 days since last rituximab therapy. First, disease (tumor) burden, absolute lymphocyte count (ALC) and time since last rituximab therapy are measured or determined for each patient. Preferred patients have a disease (tumor) burden of less than 50 cm$^2$, absolute lymphocyte count greater than $0.6 \times 10^9$/L, not less than 230 days passed since last rituximab therapy, or all of these factors. Then, the patients who have been identified as preferred patients receive the treatment using 3-(4-amino-1-oxo-1,3-dihydro-isoindol-2-yl)-piperidine-2,6-dione, or a pharmaceutically acceptable salt, solvate (e.g., hydrate) or stereoisomer thereof in an amount of about 5 to 25 mg per day.

In particular, methods of this invention encompass methods of treating or managing various forms of lymphomas such as NHL, including but not limited to, mantle cell lymphoma (MCL), follicular center lymphoma, diffuse large B-cell lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma, cutaneous B-Cell lymphoma, and any type of the mantle cell lymphomas that can be seen under the microscope (nodular, diffuse, blastic and mantle zone lymphoma). In one embodiment, the lymphoma is refractory, relapsed, or is resistant to chemotherapy other than an immunomodulatory compound of the invention.

In a separate and distinct embodiment of the invention, 3-(4-amino-1-oxo-1,3-dihydro-isoindol-2-yl)-piperidine-2,6-dione is administered in combination with another drug ("second active agent or ingredient") or another therapy for treating or managing cancer. Second active agents include small molecules and large molecules (e.g., proteins and antibodies), examples of which are provided herein, as well as stem cells or cord blood. Methods, or therapies, that can be used in combination with the administration of the compound of the invention include, but are not limited to, surgery, blood transfusions, immunotherapy, biological therapy, radiation therapy, and other non-drug based therapies presently used to treat, prevent or manage cancer.

5.1 Immunomodulatory Compounds

Compounds used in the invention include compounds that are racemic, stereomerically enriched or stereomerically pure. In some embodiments, pharmaceutically acceptable salts and solvates (e.g., hydrate) thereof are included. Preferred compounds used in the invention are small organic molecules having a molecular weight less than about 1,000 g/mol, and are not proteins, peptides, oligonucleotides, oligosaccharides or other macromolecules.

The compound used in the methods of the invention is 3-(4-amino-1-oxo-1,3-dihydro-isoindol-2-yl)-piperidine-2,6-dione (lenalidomide, also known as Revlimid® or Revimid®). The compound 3-(4-amino-1-oxo-1,3-dihydro-isoindol-2-yl)-piperidine-2,6-dione has the following chemical structure:

Specific examples of immunomodulatory compounds, include, but are not limited to, cyano and carboxy derivatives of substituted styrenes such as those disclosed in U.S. Pat. No. 5,929,117; 1-oxo-2-(2,6-dioxo-3-fluoropiperidin-3-yl)isoindolines and 1,3-dioxo-2-(2,6-dioxo-3-fluoropiperidine-3-yl) isoindolines such as those described in U.S. Pat. No. 5,874,448; the tetra substituted 2-(2,6-dioxopiperidin-3-yl)-1-oxoisoindolines described in U.S. Pat. No. 5,798,368; 1-oxo and 1,3-dioxo-2-(2,6-dioxopiperidin-3-yl)isoindolines, including, but not limited to, those disclosed in U.S. Pat. No. 5,635,517; substituted 2-(2,6-dioxopiperidin-3-yl)phthalimides and substituted 2-(2,6-dioxopiperidin-3-yl)-1-oxoisoindoles such as those described in U.S. Pat. Nos. 6,281,230 and 6,316,471; a class of non-polypeptide cyclic amides disclosed in U.S. Pat. Nos. 5,698,579 and 5,877,200; thalidomide analogs, including hydrolysis products, metabolites, and precursors of thalidomide, such as those described in U.S. Pat. Nos. 5,593,990, 5,629,327, and 6,071,948 to D'Amato; and isoindole-imide compounds such as those described in U.S. patent publication no. 2003/0096841, and International Application No. PCT/US01/50401 (International Publication No. WO 02/059106). The entireties of each of the patents and patent applications identified herein are incorporated herein by reference. Immunomodulatory compounds of the invention do not include thalidomide.

The compound of the invention can either be commercially purchased or prepared according to the methods described in the patents or patent publications disclosed herein (see e.g., U.S. Pat. No. 5,635,517, incorporated herein by reference). Further, optically pure compounds can be asymmetrically synthesized or resolved using known resolving agents or chiral columns as well as other standard synthetic organic chemistry techniques.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

The compound of the invention contains a chiral center, and thus can exist as a racemic mixture of R and S enantiomers. This invention encompasses the use of stereomerically pure forms of this compound, as well as the use of mixtures of those forms. For example, mixtures comprising equal or unequal amounts of the enantiomers may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, 1N, 1972).

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center. In other words, the invention encompasses the use of the R or S enantiomer of immunomodulatory compound in the methods.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.2 Second Active Agents

The compound of the invention can be used with or combined with other pharmacologically active compounds ("second active agents or ingredients") in methods of the invention. It is believed that certain combinations work synergistically in the treatment of particular types of lymphomas. Immunomodulatory compounds of the invention can also work to alleviate adverse effects associated with certain second active agents, and some second active agents can be used to alleviate adverse effects associated with immunomodulatory compounds of the invention.

One or more second active ingredients or agents can be used in the methods and compositions of the invention together with an immunomodulatory compound of the invention. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Typical large molecule active agents are biological molecules, such as naturally occurring or artificially made proteins. Proteins that are particularly useful in this invention include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions of the invention include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

This invention encompasses the use of native, naturally occurring, and recombinant proteins. The invention further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with compounds of the invention include monoclonal and polyclonal antibodies. Examples of antibodies include, but are not limited to, trastuzumab (Herceptin®), rituximab (Rituxan®), bevacizumab (Avastin™), pertuzumab (Omnitarg™), tositumomab (Bexxar®), edrecolomab (Panorex®), and G250. Compounds of the invention can also be combined with, or used in combination with, anti-TNF-α antibodies.

Large molecule active agents may be administered in the form of anti-cancer vaccines. For example, vaccines that secrete, or cause the secretion of, cytokines such as IL-2, G-CSF, and GM-CSF can be used in the methods, pharmaceutical compositions, and kits of the invention. See, e.g., Emens, L. A., et al., *Curr. Opinion Mol. Ther.* 3(1):77-84 (2001).

In one embodiment of the invention, the large molecule active agent reduces, eliminates, or prevents an adverse effect associated with the administration of an immunomodulatory compound of the invention. Depending on the particular immunomodulatory compound of the invention and the disease or disorder being treated, adverse effects can include, but are not limited to, drowsiness and somnolence, dizziness and orthostatic hypotension, neutropenia, infections that result from neutropenia, increased HIV-viral load, bradycardia, Stevens-Johnson Syndrome and toxic epidermal necrolysis, and seizures (e.g., grand mal convulsions). A specific adverse effect is neutropenia.

Second active agents that are small molecules can also be used to alleviate adverse effects associated with the administration of an immunomodulatory compound of the invention. However, like some large molecules, many are believed to be capable of providing a synergistic effect when administered with (e.g., before, after or simultaneously) an immunomodulatory compound of the invention. Examples of small molecule second active agents include, but are not limited to, anti-cancer agents, antibiotics, immunosuppressive agents, and steroids.

Examples of anti-cancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; bortezomib (Velcade®); brequinar sodium; bropirimine; busulfan; cactinomycin; calusterone; caracemide; carbetimer; carboplatin; carmustine; carubicin hydrochloride; carzelesin;

cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflomithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sd±1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, rituximab, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

5.3 Methods of Predicting Patient's Response and Treatment

Methods of the invention encompasses methods for identifying or screening cancer patients for treatment with 3-(4-amino-1-oxo-1,3-dihydro-isoindol-2-yl)-piperidine-2,6-dione. In particular, the methods encompass measuring one or more of the following factors: (1) disease (tumor) burden, (2) absolute lymphocyte count (ALC) and (3) time since last rituximab therapy. Then, patients having favorable values of one or more of the factors are treated with 3-(4-amino-1-oxo-1,3-dihydro-isoindol-2-yl)-piperidine-2,6-dione.

Also encompassed by the invention is a method for predicting a cancer patient's response to a therapy regimen of 3-(4-amino-1-oxo-1,3-dihydro-isoindol-2-yl)-piperidine-2,6-dione, using one or more prognostic factors of disease (tumor) burden, absolute lymphocyte count (ALC) and time since last rituximab therapy.

One embodiment of the invention encompasses a method of treating or managing a lymphoma, which comprises administering to a patient having a lymphoma a therapeutically effective amount of 3-(4-amino-1-oxo-1,3-dihydro-isoindol-2-yl)-piperidine-2,6-dione, or a pharmaceutically acceptable salt, solvate (e.g., hydrate) or stereoisomer thereof, wherein said patient meets one or more of the following criteria: (1) a disease burden of less than $50 \, cm^2$; (2) an absolute lymphocyte count greater than $0.6 \times 10^9/L$; and (3) not less than 230 days since last rituximab therapy.

First, disease (tumor) burden, absolute lymphocyte count (ALC) and time since last rituximab therapy are measured or determined for each patient. Preferred patients have a disease (tumor) burden of less than $50 \, cm^2$. Tumor burden may be estimated by the size of the largest tumor present. When estimated by the size of the largest tumor, tumor burden of $<50 \, cm^2$ can be estimated by no single tumor largest diameter greater than about 4.5 cm.

Preferred patients have absolute lymphocyte count greater than $0.6 \times 10^9/L$ or not less than 230 days passed since last rituximab therapy. The most preferred patients have all of the three factors: (1) a disease burden of less than $50 \, cm^2$; (2) an absolute lymphocyte count greater than $0.6 \times 10^9/L$; and (3) not less than 230 days since last rituximab therapy. The patients who have been identified as preferred patients receive the treatment using 3-(4-amino-1-oxo-1,3-dihydro-isoindol-2-yl)-piperidine-2,6-dione, or a pharmaceutically acceptable salt, solvate (e.g., hydrate) or stereoisomer thereof in an amount of about 5 to 25 mg per day.

In a preferred embodiment, the methods of this invention encompass methods of treating or managing various types of lymphomas by identifying preferred patients using prognostic factors. In a preferred embodiment, methods of this invention encompass methods of treating or managing various types of lymphomas such as NHL, including but not limited to, mantle cell lymphoma, MCL, follicular center lymphoma, diffuse large B-cell lymphoma, transformed lymphoma, lymphocytic lymphoma of intermediate differentiation, intermediate lymphocytic lymphoma, ILL, diffuse poorly differentiated lymphocytic lymphoma, PDL, centrocytic lymphoma, diffuse small-cleaved cell lymphoma, DSCCL, follicular lymphoma, peripheral T-cell lymphoma, cutaneous T-cell lymphoma, cutaneous B-cell lymphoma, and any type of the mantle cell lymphomas that can be seen under the microscope (nodular, diffuse, blastic and mantle zone lymphoma).

As used herein, unless otherwise specified, the term "treating" refers to the administration of a compound of the invention, or other additional active agent, after the onset of symptoms of the particular cancer. As used herein and unless otherwise indicated, the term "managing" encompasses preventing the recurrence of the particular cancer in a patient who had suffered from it, lengthening the time a patient who had suffered from the cancer remains in remission, and/or reducing mortality rates of the patients.

As used herein, the term "cancer" includes, but is not limited to, lymphomas, solid tumors (e.g., melanoma and renal cell carcinoma) and blood born tumors (e.g., multiple myeloma). The term "cancer" refers to disease of skin tissues, organs, blood, and vessels, including, but not limited to, cancers of the bladder, bone or blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus.

The term "lymphoma" refers to a heterogenous group of neoplasms arising in the reticuloendothelial and lymphatic systems. Non-Hodgkin's lymphoma (NHL) refers to malignant monoclonal proliferation of lymphoid cells in sites of the immune system, including lymph nodes, bone marrow, spleen, liver and gastrointestinal tract. The NHL includes, but is not limited to, mantle cell lymphoma (MCL), follicular center lymphoma, diffuse large B-cell lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-cell lymphoma, cutaneous B-cell lymphoma, and any type of the mantle cell lymphomas that can be seen under the microscope (nodular, diffuse, blastic and mantle zone lymphoma).

The term "relapsed" refers to a situation where patients who have had a remission of cancer after therapy have a return of lymphoid cells in the immune systems. The term "refractory or resistant" refers to a circumstance where patients, even after intensive treatment, have residual lymphoid cells in the immune systems.

This invention encompasses methods of treating patients who have been previously treated for cancer, but are non-responsive to standard therapies, as well as those who have not previously been treated. The invention also encompasses methods of treating patients regardless of patient's age, although some cancers are more common in certain age groups. The invention further encompasses methods of treating patients who have undergone surgery in an attempt to treat the cancer at issue, as well as those who have not. Because patients with cancer have heterogenous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

Methods encompassed by this invention comprise administering one or more immunomodulatory compound of the invention, or a pharmaceutically acceptable salt, solvate (e.g., hydrate), stereoisomer, clathrate, or prodrug thereof, to a patient (e.g., a human) suffering, or likely to suffer, from cancer, particularly NHL.

In one embodiment of the invention, 3-(4-amino-1-oxo-1,3-dihydro-isoindol-2-yl-piperidine-2,6-dione (Revlimid®) can be administered orally and in single or divided daily doses in an amount of from about 1 to about 50 mg/day. In a preferred embodiment, 3-(4-amino-1-oxo-1,3-dihydro-isoindol-2-yl-piperidine-2,6-dione (Revlimid®) may be administered in an amount of from about 5, 10, 15, 25, 30 or 50 mg per day, or from about 5 to about 25 mg per day. Specific doses per day include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a preferred embodiment, NHL patients are screened having a disease (tumor) burden of less than 50 cm$^2$, absolute lymphocyte count greater than $0.6\times10^9$/L, or not less than 230 days passed since last rituximab therapy. The selected patients receive 3-(4-amino-1-oxo-1,3-dihydro-isoindol-2-yl-piperidine-2,6-dione (Revlimid®) in an amount of about 25 mg per day once orally for 21 days on days 1-21, every cycle of 28 days. Patients continue therapy for 52 weeks as tolerated or until disease progression. A patient who achieves a complete response during the 52 week period receives two additional cycles of treatment prior to discontinuing treatment and entering the follow-up phase.

In a specific embodiment, 3-(4-amino-1-oxo-1,3-dihydro-isoindol-2-yl-piperidine-2,6-dione (Revlimid®) may be administered in an amount of about 25 mg per day for 21 days on days 1-21, every 28 days, to patients having mantle cell lymphoma, follicular center lymphoma, diffuse large B-cell lymphoma, or transformed lymphoma, wherein the patients meet one or more factors of the following: (1) a disease (tumor) burden of less than 50 cm$^2$, (2) absolute lymphocyte count greater than $0.6\times10^9$/L, and (3) not less than 230 days passed since last rituximab therapy. In a preferred embodiment, 3-(4-amino-1-oxo-1,3-dihydro-isoindol-2-yl-piperidine-2,6-dione (Revlimid®) is administered in the form of a capsule of 5 mg, 10 mg, 15 mg or 25 mg.

In one embodiment, the recommended starting dose of 3-(4-amino-1-oxo-1,3-dihydro-isoindol-2-yl)-piperidine-2,6-dione (Revlimid®) can be 10 mg or 25 mg per day. The dose can be escalated every week to 15, 20, 25, 30, 35, 40, 45 and 50 mg per day. The patients who experience thrombocytopenia or neutropenia that develops within or after the first four weeks of starting Revlimid® therapy may have their dosage adjusted according to a platelet count or absolute neutrophil count (ANC).

In one embodiment, 3-(4-amino-1-oxo-1,3-dihydro-isoindol-2-yl-piperidine-2,6-dione may be administered in an amount of from about 5 to about 25 mg per day to patients with various types of peripheral T-cell lymphomas such as peripheral T-cell lymphoma unspecified (PTCL-U), primary aggressive epidermotropic CD8$^+$ cytotoxic T-cell lymphoma, cutaneous γ/δ T-cell lymphoma, primary cutaneous CD4$^+$ small/medium-sized pleomorphic T-cell lymphoma, angioimmunoblastic T-cell lymphoma and anaplastic large-cell lymphoma (ALCL).

5.3.1 Combination Therapy with a Second Active Agent

Specific methods of the invention comprise administering an immunomodulatory compound of the invention, or a pharmaceutically acceptable salt, solvate (e.g., hydrate), stereoisomer, clathrate, or prodrug thereof, in combination with one or more second active agents, and/or in combination with radiation therapy, blood transfusions, or surgery. Examples of immunomodulatory compounds of the invention are disclosed herein (see, e.g., section 5.1). Examples of second active agents are also disclosed herein (see, e.g., section 5.2).

Administration of an immunomodulatory compound of the invention and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for an immunomodulatory compound of the invention is orally. Preferred routes of administration for the second active agents or ingredients of the invention are known to those of ordinary skill in the art. See, e.g., *Physicians' Desk Reference*, (2007).

In one embodiment of the invention, the second active agent is administered intravenously or subcutaneously and once or twice daily in an amount of from about 1 to about 1,000 mg, from about 5 to about 500 mg, from about 10 to about 375 mg, or from about 50 to about 200 mg. The specific amount of the second active agent will depend on the specific agent used, the type of disease being treated or managed, the severity and stage of disease, and the amount(s) of immunomodulatory compounds of the invention and any optional additional active agents concurrently administered to the patient. In a particular embodiment, the second active agent is rituximab, bortezomib, oblimersen (Genasense®), GM-CSF, G-CSF, EPO, taxotere, irinotecan, dacarbazine, transretinoic acid, topotecan, pentoxifylline, ciprofloxacin, dexamethasone, vincristine, doxorubicin, COX-2 inhibitor, IL2, IL8, IL18, IFN, Ara-C, vinorelbine, or a combination thereof.

In a specific embodiment, Revlimid® is administered in an amount of from about 5 to about 25 mg per day, in combination with rituximab in an amount of 375 mg/m$^2$ by intravenous infusion weekly. In a preferred embodiment, Revlimid® is given prior to immunosuppressive therapy to prime the immune system and then given along with it to maintain the host immune competence during the immunosuppressive therapy. The immunosupressive therapy can be rituxmab (via B-cell depletion), or other anti-cancer agents (e.g., section 5.2) known in the art which suppress B-cells and/or other cells vital to immune competence. In a preferred embodiment, Revlimid® is given in an amount of from about 5 to about 25 mg per day on days 1-21 of a 28-day cycle and rituximab is given in an amount of 375 mg/m$^2$ by intravenous infusion weekly for four weeks.

In a preferred embodiment, Revlimid® and rituximab are administered to patients with various types of non-Hodgkin's lymphomas, including, but not limited to, mantle cell lymphoma (MCL), follicular center lymphoma, diffuse large B-cell lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-cell lymphoma, cutaneous B-cell lymphoma, and mantle zone lymphoma.

In another embodiment, an immunomodulatory compound of the invention is administered alone or in combination with a second active ingredient such as vinblastine or fludarabine to patients with various types of lymphomas, including, but not limited to, Hodgkin's lymphoma, non-Hodgkin's lymphoma, cutaneous T-Cell lymphoma, cutaneous B-cell lymphoma, diffuse large B-cell lymphoma or relapsed or refractory low grade follicular lymphoma.

In another embodiment, lenalidomide is administered alone or in combination with rituximab, vinblastine or fludarabine to patients with various types of peripheral T-cell lymphomas, including, but not limited to, peripheral T-cell lymphoma unspecified (PTCL-U), primary aggressive epidermotropic CD8$^+$ cytotoxic T-cell lymphoma, cutaneous γ/δ T-cell lymphoma, primary cutaneous CD4$^+$ small/medium-sized pleomorphic T-cell lymphoma, angioimmunoblastic T-cell lymphoma and anaplastic large-cell lymphoma (ALCL).

In one embodiment, lenalidomide is administered in combination with vincristine, doxorubicin, cyclophosphamide and prednisolone (CHOP), both individually and in combination, to patients with various types of peripheral T-cell lymphomas.

In one embodiment, lenalidomide is administered in combination with prednisolone, mitoxantrone, cyclophosphamide, etoposide, bleomycin and vincristine (PMitCEBO), both individually and in combination, to patients with various types of peripheral T-cell lymphomas.

In another embodiment, GM-CSF, G-CSF or EPO is administered subcutaneously during about five days in a four or six week cycle in an amount of from about 1 to about 750 mg/m$^2$/day, preferably in an amount of from about 25 to about 500 mg/m$^2$/day, more preferably in an amount of from about 50 to about 250 mg/m$^2$/day, and most preferably in an amount of from about 50 to about 200 mg/m$^2$/day. In a certain embodiment, GM-CSF may be administered in an amount of from about 60 to about 500 mcg/m$^2$ intravenously over 2 hours, or from about 5 to about 12 mcg/m$^2$/day subcutaneously. In a specific embodiment, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In a certain embodiment, EPO may be administered subcutaneously in an amount of 10,000 Unit 3 times per week.

This invention also encompasses a method of increasing the dosage of an anti-cancer drug or agent that can be safely and effectively administered to a patient, which comprises administering to a patient (e.g., a human) an immunomodulatory compound of the invention, or a pharmaceutically acceptable derivative, salt, solvate (e.g., hydrate), or prodrug thereof. Patients that can benefit by this method are those likely to suffer from an adverse effect associated with anti-cancer drugs for treating a specific cancer of the blood, skin, subcutaneous tissue, lymph nodes, brain, lung, liver, bone, intestine, colon, heart, pancreas, adrenal, kidney, prostate, breast, colorectal, or combinations thereof. The administration of an immunomodulatory compound of the invention alleviates or reduces adverse effects which are of such severity that it would otherwise limit the amount of anti-cancer drug.

In one embodiment, an immunomodulatory compound of the invention can be administered orally and daily in an amount of from about 0.10 to about 150 mg, and preferably from about 1 to about 50 mg, more preferably from about 5 to about 25 mg prior to, during, or after the occurrence of the adverse effect associated with the administration of an anti-cancer drug to a patient. In a particular embodiment, an immunomodulatory compound of the invention is administered in combination with specific agents such as heparin, aspirin, coumadin, or G-CSF to avoid adverse effects that are associated with anti-cancer drugs such as but not limited to neutropenia or thrombocytopenia.

In another embodiment, this invention encompasses a method of treating, and/or managing lymphoma, which comprises administering an immunomodulatory compound of the invention, or a pharmaceutically acceptable salt, solvate (e.g., hydrate), stereoisomer, clathrate, or prodrug thereof, in conjunction with (e.g., before, during, or after) conventional therapy including, but not limited to, surgery, immunotherapy, biological therapy, radiation therapy, or other non-drug based therapy presently used to treat, prevent or manage cancer. The combined use of the immunomodulatory compounds of the invention and conventional therapy may provide a unique treatment regimen that is unexpectedly effective in certain patients. Without being limited by theory, it is believed that immunomodulatory compounds of the invention may provide additive or synergistic effects when given concurrently with conventional therapy.

As discussed elsewhere herein, the invention encompasses a method of reducing, treating and/or preventing adverse or undesired effects associated with conventional therapy including, but not limited to, surgery, chemotherapy, radiation therapy, hormonal therapy, biological therapy and immunotherapy. An immunomodulatory compound of the invention and other active ingredient can be administered to a patient prior to, during, or after the occurrence of the adverse effect associated with conventional therapy.

In one embodiment, an immunomodulatory compound of the invention can be administered in an amount of from about 0.10 to about 150 mg, and preferably from about 1 to about 50 mg, more preferably from about 5 to about 25 mg orally and daily alone, or in combination with a second active agent disclosed herein (see, e.g., section 5.2), prior to, during, or after the use of conventional therapy.

5.3.2 Use with Transplantation Therapy

Compounds of the invention can be used to reduce the risk of Graft Versus Host Disease (GVHD). Therefore, the invention encompasses a method of treating and/or managing cancer, particularly NHL, which comprises administering the immunomodulatory compound of the invention, or a pharmaceutically acceptable salt, solvate (e.g., hydrate), stereoisomer, clathrate, or prodrug thereof, in conjunction with transplantation therapy.

As those of ordinary skill in the art are aware, the treatment of cancer is often based on the stages and mechanism of the disease. For example, as inevitable leukemic transformation develops in certain stages of cancer, transplantation of peripheral blood stem cells, hematopoietic stem cell preparation or bone marrow may be necessary. The combined use of the immunomodulatory compound of the invention and transplantation therapy provides a unique and unexpected synergism. In particular, an immunomodulatory compound of the invention exhibits immunomodulatory activity that may provide additive or synergistic effects when given concurrently with transplantation therapy in patients with cancer.

An immunomodulatory compound of the invention can work in combination with transplantation therapy reducing complications associated with the invasive procedure of transplantation and risk of GVHD. This invention encompasses a method of treating and/or managing cancer which comprises administering to a patient (e.g., a human) an immunomodulatory compound of the invention, or a pharmaceutically acceptable salt, solvate (e.g., hydrate), stereoisomer, clathrate, or prodrug thereof, before, during, or after the transplantation of umbilical cord blood, placental blood, peripheral blood stem cell, hematopoietic stem cell preparation or bone marrow. Examples of stem cells suitable for use in the methods of the invention are disclosed in U.S. patent publication nos. 2002/0123141, 2003/0235909 and 2003/0032179, by R. Hariri et al., the entireties of which are incorporated herein by reference.

In one embodiment of this method, 3-(4-amino-oxo-1,3-dihydro-isoindol-2-yl)-piperidine-2,6-dione (Revlimid®) is administered to patients with NHL before, during, or after the transplantation of autologous peripheral blood progenitor cell.

In another embodiment, 3-(4-amino-oxo-1,3-dihydro-isoindol-2-yl)-piperidine-2,6-dione (Revlimid®) is administered to patients with relapsed NHL after the stem cell transplantation.

5.3.3 Cycling Therapy

In certain embodiments, the therapeutic agents of the invention are cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, in one specific embodiment of the invention, an immunomodulatory compound of the invention is administered daily in a single or divided doses in a four to six week cycle with a rest period of about a week or two weeks. The invention further allows the frequency, number, and length of dosing cycles to be increased. Thus, another specific embodiment of the invention encompasses the administration of an immunomodulatory compound of the invention for more cycles than are typical when it is administered alone. In yet another specific embodiment of the invention, an immunomodulatory compound of the invention is administered for a greater number of cycles that would typically cause dose-limiting toxicity in a patient to whom a second active ingredient is not also being administered.

In one embodiment, an immunomodulatory compound of the invention is administered daily and continuously for three or four weeks at a dose of from about 0.10 to about 150 mg/d followed by a break of one or two weeks. In a particular embodiment, an immunomodulatory compound of the invention is administered in an amount of from about 1 to about 50 mg/day, preferably in an amount of about 25 mg/day for three to four weeks, followed by one week or two weeks of rest in a four or six week cycle.

In a preferred embodiment, 3-(4-amino-oxo-1,3-dihydro-isoindol-2-yl)-piperidine-2,6-dione (Revlimid®) is administered to patients with various types of lymphomas who have values of a disease (tumor) burden of less than 50 cm$^2$, absolute lymphocyte count greater than $0.6 \times 10^9$/L, or not less than 230 days passed since last rituximab therapy, in an amount of about 10 mg, 15 mg, 20 mg, 25 mg or 30 mg per day for 21 days followed by seven days rest in a 28 day cycle. In the most preferred embodiment, 3-(4-amino-oxo-1,3-dihydro-isoindol-2-yl)-piperidine-2,6-dione (Revlimid®) is administered to patients with refractory or relapsed aggressive NHL having favorable values of the prognostic factors, in an amount of about 25 mg per day for 21 days followed by seven days rest in a 28 day cycle.

In one embodiment of the invention, an immunomodulatory compound of the invention and a second active agent or ingredient are administered orally, with administration of an immunomodulatory compound of the invention occurring 30 to 60 minutes prior to a second active ingredient, during a cycle of four to six weeks. In another embodiment of the invention, an immunomodulatory compound of the invention is administered orally and a second active ingredient is administered by intravenous infusion.

In a specific embodiment, one cycle comprises the administration of from about 10 to about 25 mg/day of Revlimid® and from about 50 to about 750 mg/m$^2$/day of a second active ingredient daily for three to four weeks and then one or two weeks of rest.

In one embodiment, rituximab can be administered in an amount of 375 mg/m$^2$ weekly by intravenous infusion to patients with various types of NHL such as mantle cell lymphoma, follicular lymphoma and diffuse large cell lymphoma. In a preferred embodiment, rituximab can be administered in an amount of 375 mg/m$^2$ weekly by intravenous infusion to patients with refractory or relapsed aggressive NHL.

Typically, the number of cycles will be from about one to about 24 cycles, more typically from about two to about 16 cycles, and even more typically from about four to about 13 cycles.

6. EXAMPLES

Certain embodiments of the invention are illustrated by the following non-limiting example.

6.1 Clinical Studies in Patients

Clinical Study 1

A multi-center, open-label, Phase II study was conducted in patients with relapsed and refractory aggressive non-Hodgkin's lymphoma (NHL). The trial was designed for oral monotherapy with 3-(4-amino-1-oxo-1,3-dihydro-isoindol-2-yl)-piperidin-2,6-dione (Revlimid® or lenalidomide) in 49 patients with relapsed and refractory aggressive NHL following one or more prior treatment regimen with measurable disease. Patients in the study received lenalidomide in an amount of 25 mg orally once daily for days one to 21 in a 28-day cycle and continued therapy for 52 weeks as tolerated or until disease progression. A patient who achieved a complete response during the 52 week period was to receive two additional cycles of treatment prior to discontinuing treatment and entering the follow-up phase.

The patients age 23 to 86 years (median age 65), with relapsed and refractory aggressive NHL. (Table 1. Patient demographics).

TABLE 1

Patient demographics

| Patient characteristics | n |
|---|---|
| Median age, years (range) | 65 (23-86) |
| Number of females, (%) | 24 (49) |
| Median time from diagnosis, years (range) | 2.7 (0.4-32) |
| Median number prior treatment regimens (range) | 4 (1-7) |
| Rituximab refractory, (%) | 27 (63) |
| Median tumor burden, $cm^2$ (range) | 25 (3-335) |
| Histology, (%) | |
| Diffuse large B-cell lymphoma | 26 (53) |
| Follicular center lymphoma grade 3 | 5 (10) |
| Mantle cell lymphoma | 15 (30) |
| Transformed | 3 (6) |
| International Prognostic Index, (%) | |
| 0-1 | 8 (16) |
| 2 | 22 (45) |
| 3 | 13 (26) |
| 4-5 | 6 (12) |
| Prior stem cell transplant, (%) | |
| Yes | 14 (29) |
| No | 34 (69) |
| Missing | 1 (2) |

The patients who had received a median of 4 prior treatments (range: 1-7 prior treatments), were administered with lenalidomide in an amount of 25 mg orally once daily for 21 days in the treatment cycle of 28 days. Of the 49 patients, 26 had diffuse large cell lymphoma, 15 had mantle cell lymphoma, five patients had follicular lymphoma, and three had transformed lymphoma. Median time from diagnosis was 2.7 years (range 0.4-32) and patients had received a median of 4 (range 1-8) prior drug regimens for NHL. Ninety-three percent of the patients had received prior rituximab and 63% of the patients were rituximab refractory. Twenty-nine percent of the patient's had a prior stem cell transplant.

Seventeen patients had an objective response (Table 2. Efficacy by histology type). Responses were seen in each of the aggressive histologic subtypes studied.

TABLE 2

Objective response of patients receiving lenalidomide therapy by histology type

| Histology | n | CR | CRu | PR | SD | PD | RR, % |
|---|---|---|---|---|---|---|---|
| Aggressive | 49 | 2 | 4 | 11 | 11 | 21 | 35 |
| DLBCL | 26 | 1 | 2 | 2 | 7 | 14 | 19 |
| FCL | 5 | 0 | 1 | 2 | 0 | 2 | 60 |
| MCL | 15 | 1 | 1 | 6 | 2 | 5 | 53 |
| TSF | 3 | 0 | 0 | 1 | 2 | 0 | 33 |

Note:
CR, complete response;
CRu, complete response unconfirmed;
DLBCL, diffuse large B-cell lymphoma;
FCL, follicular-center lymphoma;
MCL, mantle cell lymphoma;
PR, partial response;
RR, response rate;
SD, stable disease;
PD, progressive disease;
TSF, transformed lymphoma.

Fourteen patients had stable disease at the first (cycle 2) assessment and three of these (21%) went on to exhibit a response (1 CRu, 2 PP) with continued treatment. Likewise four patients with an initial response of PR at 2 cycles went on to CR/CRu with continued treatment. Overall, seven (25%) of the 28 patients with SD or PR at first assessment improved their response with continued treatment.

The response to lenalidomide was not dependent upon IPI or its individual components of age, disease stage, ECOG, number of extra nodal sites, or elevated LDH. Likewise, the response was independent of a patient's number of prior therapies and sex. The response to lenalidomide was the same for patients who were refractory to rituximab and those who were not (30% vs. 31%). Of the four patients of the 49 who were rituximab naïve, two patients had CR, 1 patient had PR and 1 patient had SD.

However, the response to lenalidomide was dependent upon a patient's disease burden, absolute lymphocyte count and time since last rituximab therapy. The response to lenalidomide was dependent upon the patient's tumor burden (<50 $cm^2$ vs. >=50 $cm^2$: 52% vs. 0% (p=0.0003). The results indicate that patients who had tumor burden of less than 50 $cm^2$ had a higher likelihood of response (p=0.0003). The response to lenalidomide was also dependent upon the patient's tumor burden as estimated by the largest tumor lesion (<=4.5 cm vs. >4.5 cm: 55% vs. 5% (p=0.0005). The results indicate that patients whose largest lesion was no greater than 4.5 cm had a higher likelihood of response (p=0.001). The factor can be a prognostic factor for response in patients with non-Hodgkin's lymphoma.

The response to lenalidomide was also dependent upon absolute lymphocyte count (>0.6×$10^9$/L vs. <=0.6×$10^9$/L: 42% vs. 9% (p=0.07). The results indicate that patients who had absolute lymphocyte count greater than 0.6×$10^9$/L had a higher likelihood of response (p=0.07). This factor can be an independent predictive factor for response in patients with non-Hodgkin's lymphoma.

Further, the response to lenalidomide was dependent upon days passed since last rituximab therapy (>=230 days vs. <230 days: 52% vs. 6% (p=0.001). Time from last rituximab therapy was evaluated to exclude the possibility that responses to lenalidomide were related to residual rituximab due to its relatively long half-life. The results indicate that patients who had rituximab not less than 230 days before beginning administration of lenalidomide had a higher likelihood of response (p=0.001). Rituximab produces immune suppression by depleting the hosts normal B-cells. The kinetics of B-cell repopulation and restoration of the host immune competence is approximately 230 days at which time lenalidomide is again active.

Patients with favorable values for these prognostic factors of disease burden, absolute lymphocyte count and time since last rituximab therapy (n=23) had a response rate of 65%, while patients with unfavorable values for these prognostic values (n=26) had a response rate of 8% (p=0.0001). Thus, these factors are used to predict responses of patients to therapy for NHL.

Figure 1:
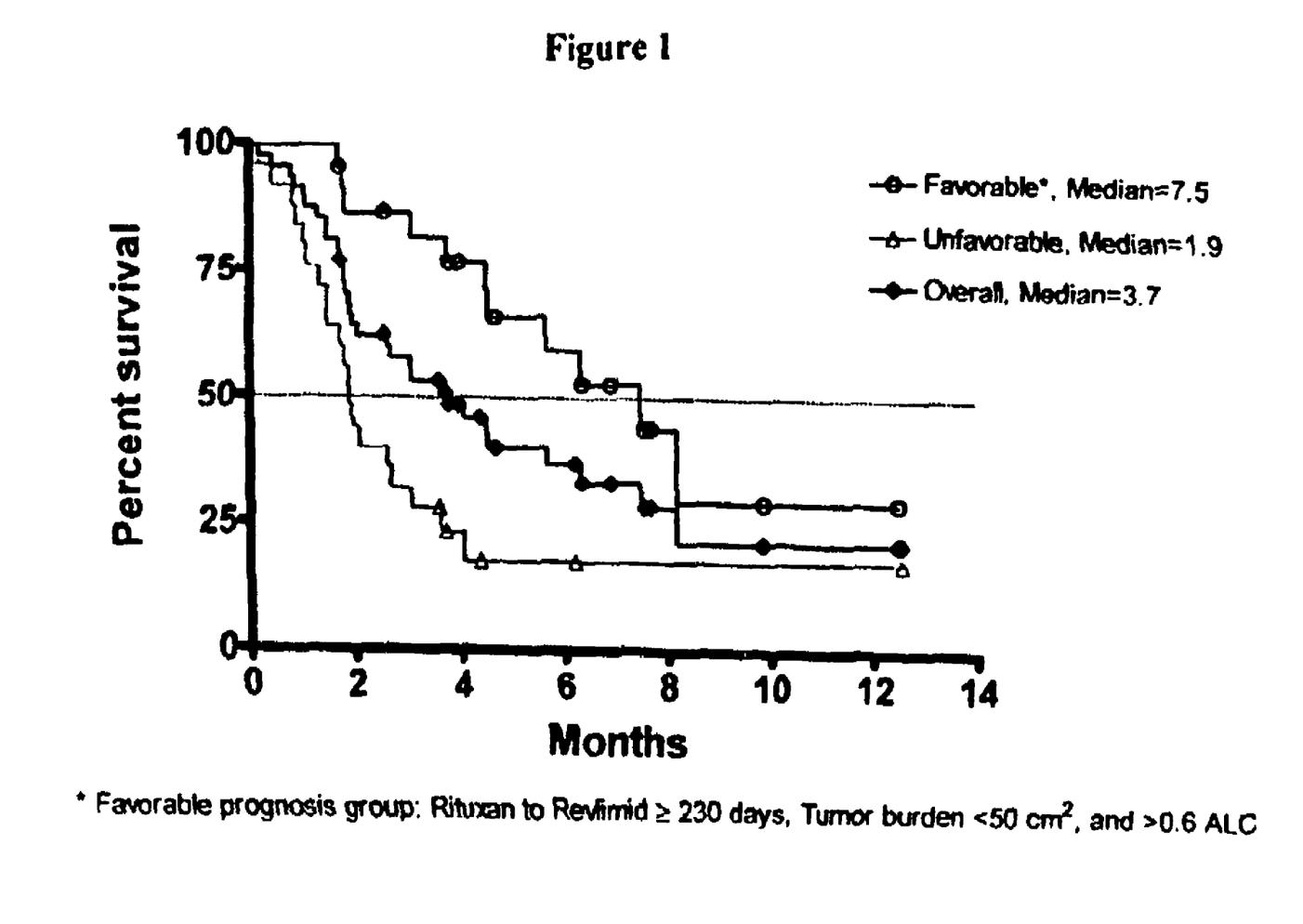
FIG. 1 represents Kaplan-Meier progression-free survival curve. It shows the progression free survival for all patients, patients with favorable and unfavorable prognostic values. Median progression-free survival was 3.7 months for the whole group, 7.5 months for patients with favorable prognostic values, and 1.9 months for patients with poor prognostic factors.

FIG. 1 shows the progression free survival for all patients, patients with favorable and unfavorable prognostic values. Median progression-free survival was 3.7 months for the whole group, 7.5 months for patients with favorable prognostic values and 1.9 months for patients with poor prognostic factors. (FIG. 1. Kaplan-Meier progression-free survival curve).

Clinical Study 2

In a separate clinical study, 86 patients received at least 25 mg of lenalidomide once daily on Days 1-21 every 28 days and continued therapy as tolerated or until disease progression. Forty-eight of these patients were evaluable for response assessment (Table 3). The median age was 65 years. The most common histology was DLBCL (63%). The median time from diagnosis to lenalidomide treatment was 2 years.

Patients received a median of 4 prior treatment regimens for NHL. Median time from last rituximab treatment was 297 days. 48% of the patients had a prior stem cell transplant. Ninety-six percent of the patients had received prior rituximab.

TABLE 3

Patient Demographics and Baseline Characteristics[1]

| Patient characteristics | (N = 48) |
|---|---|
| Median age, years (range) | 65.5 (21-84) |
| Males, n (%) | 36 (75) |
| Median time from diagnosis, years (range) | 2 (0.2-12) |
| Median number prior treatment regimens, n (range) | 4 (1-13) |
| Median tumor burden, cm$^2$ (range) | 25.2 (2-337)[2] |
| Median time from last rituximab treatment, days (range) | 297 (48-2204)[4] |
| Histology, n (%) | |
| Diffuse large B-cell lymphoma | 30 (63) |
| Mantle cell lymphoma | 14 (29) |
| Transformed | 3 (6) |
| Follicular center lymphoma | 1 (2) |
| Prior stem cell transplantation, n (%) | 23 (48) |

[1]All patients evaluable for response assessment
[2]Data missing for 1 patient
[3]Data missing for 2 patients; four patients did not received prior rituximab
[4]Data missing for 4 patients; two patients did not received prior rituximab The overall response rate (ORR) was 27% (Table 4). One patient had a complete response, 12 patients had partial response, and 10 patients had stable disease.

TABLE 4

Objective Response of Patients by Histology Type

| Histology | No. of patients | CR | Cru | PR | SD | PD | ORR (%) |
|---|---|---|---|---|---|---|---|
| Aggressive NHL | 48 | 1 | | 12 | 10 | 25 | 27 |
| Diffuse large B-cell | 30 | 1 | | 5 | 5 | 19 | 20 |
| Follicular center lymphoma grade 3 | 1 | 0 | | 1 | 0 | 0 | 100 |
| Mantle cell lymphoma | 14 | 0 | | 5 | 4 | 9 | 36 |
| Transformed lymphoma | 3 | 0 | | 1 | 1 | 1 | 33 |

Abbreviations:
CR, complete response;
Cru, unconfirmed CR;
PR, partial response;
SD, stable disease;
PD, progressive disease;
ORR, overall response rate;
NHL, non-Hodgkin's lymphoma.

Response to lenalidomide was associated with low tumor burden (33% for <50 cm$^2$ v 14% for ≧50 cm$^2$), and longer time from rituximab to lenalidomide treatment (46% for ≧230 days v 5% for <230 days). Patients with favorable values for both of these factors (N=19) had a 53% ORR, compared with a 10% ORR for patients with unfavorable values (N=29).

These results from Study 2 confirm the results of Study 1 in that: lenalidomide monotherapy has activity with manageable hematological side effects in aggressive NHL, and that tumor burden and time since last rituximab dose are factors that predict the response of aggressive NHL to lenalidomide monotherapy activity. Taken together, the results of the studies indicate that lenalidomide produces a 31% response rate with a duration of approximately 6 months with manageable hematological side effects, and that patients with favorable values for both tumor burden and time since last rituximab treatment (N=43) had a 60% ORR compared with a 7.4% ORR for patients with unfavorable values for the predictive factors (N=54) (Table 5).

TABLE 5

Response Rates for Predictive Factors in Study 1 and 2

| Predictive Factors | Number of patients | Responders | Response Rate |
|---|---|---|---|
| Tumor burden[1] | | | |
| <50 cm$^2$ | 66 | 28 | 42% |
| ≧50 cm$^2$ | 29 | 2 | 6.9% |
| Time from rituximab | | | |
| ≧230 days | 57 | 28 | 49% |
| <230 days | 40 | 2 | 5% |
| Two Variables[1] | | | |
| Favorable | 43 | 26 | 60% |
| Unfavorable | 54 | 4 | 7.4% |

[1]Tumor measurements were missing for two patients (one in Study 1 and one in Study 2)
Favorable = patients with tumor burden, <50 cm$^2$ and time since last dose of rituximab ≧230 days.
Unfavorable = patients with tumor burden ≧50 cm$^2$ and/or time since last dose of rituximab <230 days.

Clinical Study 3

A multi-center, open label, phase II study was conducted to evaluate the efficacy of 3-(4-amino-1-oxo-1,3-dihydro-isoindol-2-yl)-piperidin-2,6-dione (lenalidomide) for peripheral T-cell lymphomas (PTCL). Patients with relapsed or refractory disease were eligible, as well as patients who had not previously had systemic therapy but who were ineligible for standard curative chemotherapy regimens due to comorbid illness. Each cycle (28 days) of treatment comprises administration of about 25 mg of 3-(4-amino-1-oxo-1,3-dihydro-isoindol-2-yl)-piperidin-2,6-dione (lenalidomide) given orally daily for 21 days followed by 7 days of rest, until disease progression, death or unacceptable toxicity.

Ten (9 males and 1 female) patients were enrolled. Median age of participants was 56 years (range, 42-76 years). Histologies of the patients included PTCL unspecified (n=4), angioimmunoblastic T-cell lymphoma (n=4), anaplastic large cell lymphoma (n=1), and gamma/delta T-cell lymphoma (n=1). Median number of prior lines of systemic therapy was one (range, 0-3). Median number of cycles was two (range, 1-8).

Therapy has generally been well tolerated. The study result shows that lenalidomide is effective in treating peripheral T-cell lymphomas, particularly relapsed or refractory peripheral T-cell lymphomas.

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method for treating a lymphoma in a human, comprising:
   a) measuring a patient's disease burden, an absolute lymphocyte count or time since last rituximab therapy;
   b) selecting a patient who has a disease burden of less than 50 cm$^2$, an absolute lymphocyte count greater than 0.6× 10$^9$/L, or not less than 230 days since last rituximab therapy; and c) administering a therapeutically effective amount of 3-(4-amino-1-oxo-1,3-dihydro-isoindol-2-yl)-piperidine-2,6-dione to the patient.

2. The method of claim 1, wherein the patient has two or more of the following: a disease burden of less than 50 cm$^2$, an absolute lymphocyte count greater than 0.6×10$^9$/L, or not less than 230 days since last rituximab therapy.

3. The method of claim 1, wherein the patient has all of the following: a disease burden of less than 50 cm$^2$, an absolute lymphocyte count greater than 0.6×10$^9$/L, and not less than 230 days since last rituximab therapy.

4. The method of claim 1, wherein the patient is refractory to rituximab.

5. The method of claim 1, wherein the patient has not been treated with rituximab.

6. The method of claim 1, wherein the lymphoma is relapsed, refractory or resistant to conventional therapy.

7. The method of claim 1, wherein the lymphoma is non-Hodgkin's lymphoma.

8. The method of claim 1, wherein the lymphoma is mantle cell lymphoma, follicular center lymphoma, diffuse large B-cell lymphoma, transformed lymphoma, lymphocytic lymphoma of intermediate differentiation, intermediate lymphocytic lymphoma, diffuse poorly differentiated lymphocytic lymphoma, centrocytic lymphoma, diffuse small-cleaved cell lymphoma, peripheral T-cell lymphoma, cutaneous T-cell lymphoma, cutaneous B-cell lymphoma, or mantle zone lymphoma.

9. The method of claim 1, wherein the amount of 3-(4-amino-oxo-1,3-dihydro-isoindol-2-yl)-piperidine-2,6-dione administered is about 10, 15, 20 or 25 mg per day.

10. The method of claim 1, wherein the amount of 3-(4-amino-oxo-1,3-dihydro-isoindol-2-yl)-piperidine-2,6-dione administered is about 25 mg per day.

11. The method of claim 1, wherein 3-(4-amino-oxo-1,3-dihydro-isoindol-2-yl)-piperidine-2,6-dione administered is enantiomerically pure.

12. The method of claim 11, wherein 3-(4-amino-oxo-1,3-dihydro-isoindol-2-yl)-piperidine-2,6-dione administered is S enantiomer.

13. The method of claim 11, wherein 3-(4-amino-oxo-1,3-dihydro-isoindol-2-yl)-piperidine-2,6-dione administered is R enantiomer.

14. The method of claim 1, wherein 3-(4-amino-oxo-1,3-dihydro-isoindol-2-yl)-piperidine-2,6-dione is administered orally.

15. The method of claim 14, wherein 3-(4-amino-oxo-1,3-dihydro-isoindol-2-yl)-piperidine-2,6-dione is administered in the form of a capsule.

16. The method of claim 15, wherein 3-(4-amino-oxo-1,3-dihydro-isoindol-2-yl)-piperidine-2,6-dione is administered in the form of a capsule of 5 mg, 10 mg, 15 mg or 25 mg.

17. The method of claim 1, wherein 3-(4-amino-oxo-1,3-dihydro-isoindol-2-yl)-piperidine-2,6-dione is administered for 21 days followed by seven days rest in a 28 day cycle.

18. The method of claim 17 wherein 3-(4-amino-oxo-1,3-dihydro-isoindol-2-yl)-piperidine-2,6-dione is administered in an amount of about 25 mg per day for 21 days followed by seven days rest in a 28 day cycle.

19. The method of claim 18, further comprising administration of the compound for 52 weeks as tolerated or until disease progression.

20. The method of claim 19, further comprising administering the compound to a patient who achieves a complete response for two additional cycles.

21. The method of claim 1, further comprising administering a therapeutically effective amount of a second active agent.

22. The method of claim 21, wherein the second active agent is an antibody, a hematopoietic growth factor, a cytokine, an anti-cancer agent, an antibiotic, a cox-2 inhibitor, an immunomodulatory agent, an immunosuppressive agent, or a corticosteroid.

23. The method of claim 1, wherein 3-(4-amino-oxo-1,3-dihydro-isoindol-2-yl)-piperidine-2,6-dione is administered before administering rituximab.

24. The method of claim 1, wherein 3-(4-amino-oxo-1,3-dihydro-isoindol-2-yl)-piperidine-2,6-dione is administered before administering immune suppressive agents.

25. The method of claim 1, wherein the disease burden is estimated by no single tumor with diameter greater than 4.5 cm.

* * * * *